(12) United States Patent
Da Silva et al.

(10) Patent No.: US 7,749,260 B2
(45) Date of Patent: Jul. 6, 2010

(54) DEVICES AND METHODS FOR TREATMENT OF SKIN CONDITIONS

(76) Inventors: Luiz B. Da Silva, 1995 Camino Ramon Pl., Danville, CA (US) 94526; George Choi, 3239 Oak Knoll Dr., Redwood City, CA (US) 94062; Joseph Neev, 950 Acapulco St., Laguna Beach, CA (US) 92651

( * ) Notice: Subject to any disclaimer, the term of this patent is extended or adjusted under 35 U.S.C. 154(b) by 346 days.

(21) Appl. No.: 11/299,284

(22) Filed: Dec. 9, 2005

(65) Prior Publication Data

US 2006/0142750 A1 Jun. 29, 2006

Related U.S. Application Data

(63) Continuation-in-part of application No. 11/216,595, filed on Aug. 30, 2005, now Pat. No. 7,494,492.

(60) Provisional application No. 60/634,904, filed on Dec. 10, 2004, provisional application No. 60/653,740, filed on Feb. 16, 2005.

(51) Int. Cl.
*A61F 7/00* (2006.01)
(52) U.S. Cl. .............. 607/96; 607/98; 607/99
(58) Field of Classification Search ............. 606/41–50; 607/96, 98–99
See application file for complete search history.

(56) References Cited

U.S. PATENT DOCUMENTS

| | | | |
|---|---|---|---|
| 4,449,528 A * | 5/1984 | Auth et al. ............. | 606/31 |
| 4,860,744 A * | 8/1989 | Johnson et al. .......... | 606/31 |
| 5,593,406 A | 1/1997 | Eggers et al. | |
| 5,830,211 A | 11/1998 | Santana et al. | |
| 6,066,153 A | 5/2000 | Lev | |
| 6,162,211 A | 12/2000 | Tankovich et al. | |

(Continued)

FOREIGN PATENT DOCUMENTS

WO  WO 89/04137  5/1989

(Continued)

OTHER PUBLICATIONS

European Search Report for PCT/US2005044547, mailed Apr. 23, 2008, 7 pgs.

(Continued)

*Primary Examiner*—Roy D Gibson
(74) *Attorney, Agent, or Firm*—Schnader Harrison Segal & Lewis LLP

(57) ABSTRACT

Devices and methods for the treatment of skin conditions and lesions are disclosed herein. One aspect of the invention is a compact hand held device that can be safely used by those suffering from skin conditions, such as acne, warts, cold blisters, blemished skin, or fine wrinkles. The devices described herein employ the application of heat for the treatment of skin conditions and lesions. Typically, the peak temperatures employed are about 70° C. to about 400° C. by the devices, are achieved in less than about 1 second, and maintained for less than about 1 second. In some embodiments, the skin surface is heated with heat pulses. Thermal conduction transfers heat from the device to the skin and causes a biological response that accelerates acne clearing, treats blemished skin, itching, or fine wrinkles. The total heat transferred is low enough to prevent burns.

7 Claims, 4 Drawing Sheets

U.S. PATENT DOCUMENTS

| | | | |
|---|---|---|---|
| 6,176,856 B1 | 1/2001 | Jandak et al. | |
| 6,228,078 B1 * | 5/2001 | Eggers et al. | 606/32 |
| 6,235,027 B1 | 5/2001 | Herzon | |
| 6,245,093 B1 | 6/2001 | Li et al. | |
| 6,635,075 B2 | 10/2003 | Li et al. | |
| 6,740,085 B2 | 5/2004 | Hareyama et al. | |
| 7,137,979 B2 | 11/2006 | Conrad et al. | |
| 7,170,034 B2 * | 1/2007 | Shalev et al. | 219/223 |
| 2004/0127962 A1 | 7/2004 | Li et al. | |
| 2004/0167592 A1 * | 8/2004 | Grove et al. | 607/96 |
| 2005/0203596 A1 | 9/2005 | Li et al. | |
| 2005/0288748 A1 | 12/2005 | Li et al. | |
| 2006/0129214 A1 | 6/2006 | Da Silva et al. | |

FOREIGN PATENT DOCUMENTS

| | | |
|---|---|---|
| WO | WO 96/35469 | 11/1996 |

OTHER PUBLICATIONS

Bruce, et al. Significant efficacy and safety of low level intermittent heat in patients with mild to moderate acne. Jun. 2005. Available at http://www.myzeno.com/doc/zenowhite.pdf.

Elman, et al. The role of pulsed light and heat energy (LHE) in acne clearance. J Cosmet Laser Ther. 2004; 6(2):91-5.

Gold, et al. The use of a novel intense pulsed light an dheat source and ALA-PDT in the treatment of moderate to severe inflammatory acne vulgaris. J. Drugs Dermatol. 2004; 3(6):S15-19.

Henriques, F. C. Studies of thermal injury: the predictability and the significance of thermally induced rate processes leading to irreversible epidermal injury. Arhives of Pathology. 1947; 43(5):489-502.

Paithankar, et al. Acne threatment with a 1,450 nm wavelength laser and cryogen spray cooling. Lasers in Surgery and Medicine. 2002; 31:106-114.

Ruiz-Esparza, et al. Nonablative radiofrequency for active acne vulgaris: the use of deep dermal heat in the treatment of moderate to severe active acne vulgaris (thermotherapy): a report of 22 patients. Dermatol Surg. 2003; 29(4):333-9.

Tye, et al. Acne treated wtih compress and a corticosteroid cream. Archives of Dermatology. 1964; 89:201-203.

Office Action dated Sep. 21, 2006 for U.S. Appl. No. 11/216,595.

Response to Sep. 21, 2006 Office Action dated Nov. 14, 2006 for U.S. Appl. No. 11/216,595.

Office Action dated Feb. 12, 2007 for U.S. Appl. No. 11/216,595.

Response to Feb. 12, 2007 Office Action dated May 15, 2007 for U.S. Appl. No. 11/216,595.

Office Action dated Aug. 7, 2007 for U.S. Appl. No. 11/216,595.

Response to Aug. 7, 2007 Office Action dated Oct. 7, 2007 for U.S. Appl. No. 11/216,595.

Final Office Action dated Dec. 26, 2007 for U.S. Appl. No. 11/216,595.

Response to Dec. 26, 2007 Final Office Action dated Mar. 10, 2008 for U.S. Appl. No. 11/216,595.

Office Action dated Mar. 31, 2008 for U.S. Appl. No. 11/216,595.

Response to Mar. 31, 2008 Office Action dated Apr. 19, 2008 for U.S. Appl. No. 11/216,595.

Office Action dated Aug. 7, 2008 for U.S. Appl. No. 11/216,595.

Response to Aug. 7, 2008 Office Action dated Aug. 21, 2008 for U.S. Appl. No. 11/216,595.

Notice of Allowance dated Nov. 25, 2008 for U.S. Appl. No. 11/216,595.

First Office Action dated Mar. 27, 2009 for Chinese Patent Application No. 200580042909.1.4.

International Search Report dated Nov. 22, 2006 for PCT Patent Application No. PCT/US05/44547.

* cited by examiner

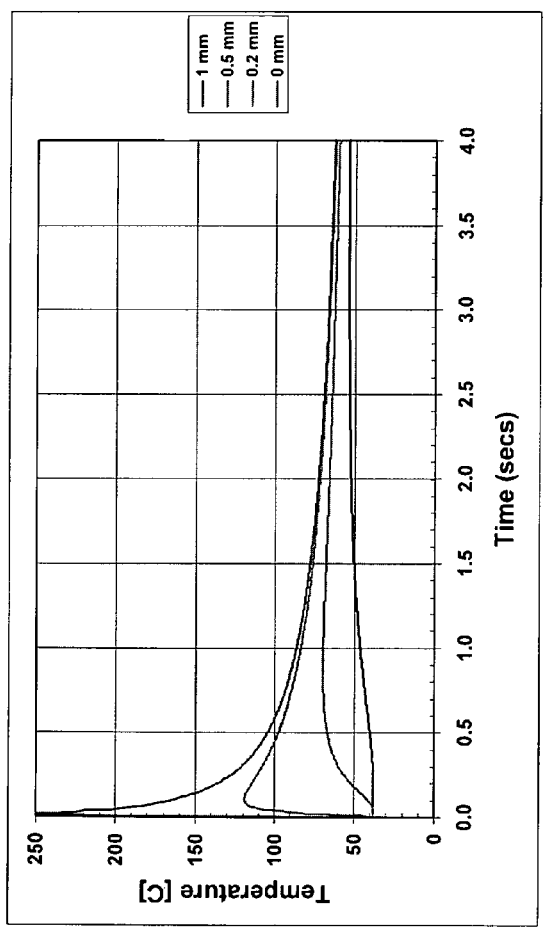
Figure 8 Temperature time history at different tissue depths from surface for a single heating pulse
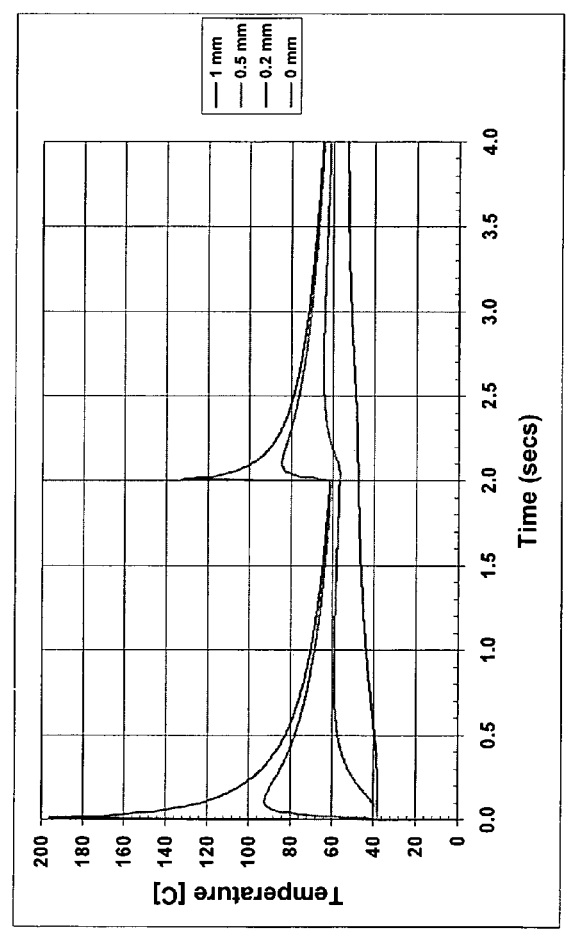
Figure 9 Temperature time history at different tissue depths from surface for two heating pulses (0 and 2.0 secs) with the same total energy as Figure 8.

DEVICES AND METHODS FOR TREATMENT OF SKIN CONDITIONS

CROSS-REFERENCE

This is a continuation-in-part of U.S. patent application Ser. No. 11/216,595, titled: "Skin Treatment Device" filed Aug. 30, 2005, now U.S. Pat. No. 7,494,492 incorporated herein by reference. This application claims priority to U.S. Provisional Patent Application Ser. No. 60/634,904, titled "Skin Treatment Device," filed Dec. 10, 2004 and U.S. Provisional Patent Application Ser. No. 60/653,740, titled "Skin Rejuvenation Device," filed Feb. 16, 2005; both incorporated herein by reference.

BACKGROUND OF THE INVENTION

Acne affects more than 90% of all adolescents, nearly 50% of all adult women and 25% of all adults. One of the main causes of acne is improper drainage of a hair follicle caused by a plug of dead cells or dirt that trap oil and bacteria. The hair follicle opening is approximately 50 μm to about 100 μm in diameter. The opening of any other pore on the skin is substantially smaller. In particular, the opening of a sweat pore is less than about 30 μm in diameter.

There are a variety of ways to treat acne. Benzoyl peroxide is one of the most commonly used ingredients in over-the-counter treatments, and it can be very effective in treating mild cases of non-inflammatory acne. It is safe for children as well as adults, and may be combined with other topical or oral treatments. For patients who suffer from moderate to severe acne, doctors may prescribe a combination of topical remedies and oral antibiotics. The most common oral medications used to treat acne are tetracycline, minocycline, doxycycline and erythromycin.

Alternatives to medication include UV light radiation, laser treatment, or abrasion. Most of these systems are large and in most cases require professional treatment. U.S. Pat. No. 6,635,075 by Li et al. describes a heating device that can also be used to treat acne. The device described therein uses a heater and temperature sensor to maintain a constant temperature surface that can be applied to skin. In order to prevent burns during the long application time (minutes), the maximum temperature allowed is about 62° C. The long treatment time makes this device impractical for normal acne treatment. A need exists for a compact device that can be used effectively and quickly to treat acne. The present invention fulfills this need, and further provides related advantages.

Methods of rejuvenating skin range from the aggressive face lift surgery and skin resurfacing by lasers (for example, using $CO_2$ lasers) or chemical peel, to the less effective non-ablative lasers systems, RF energy skin rejuvenation systems, microdermabrasion, other abrasive devices as well as various lotions and creams. Additional alternative methods include the application of UV, infrared and light radiation, laser treatment, mechanical abrasion or ultrasound energy. Most of these systems are large and in most cases require professional treatment. A need exists for effective skin rejuvenation devices.

SUMMARY OF THE INVENTION

It is an object of the present invention to provide devices and methods for treating skin conditions and skin lesions, such as acne, removing fine wrinkles and clearing skin. Another object of the present invention is to provide a hand held device that can be safely used to heat tissue without causing a burn. These and other objects will be apparent to those skilled in the art based on the teachings herein.

One aspect of the invention provides a device for treatment of skin conditions including a heating element adapted and configured to contact a skin surface; and a controller adapted and configured to automatically heat the heating element to a temperature of at least about 70° C. in a period of less than about one second and to maintain the heating element at a temperature of at least about 70° C. for a period of less than one second in response to a user input. In some embodiments, the controller is further adapted to cease heating the heating element and to reheat the heating element without a further user input. The heating element and controller may be located in a housing, with the housing being capable of being held in a hand of a user.

Another aspect of the invention provides a device for treatment of skin conditions including a housing adapted and configured to be held in a hand of a user, with the housing including a heating element adapted to contact a skin surface; a controller adapted and configured to automatically heat the heating element to a temperature of at least about 70° C. in a period of less than about one second and to maintain a temperature of at least about 70° C. for a period of less than one second in response to a user input; and a user interface adapted and configured to be activated by a user to provide the user input. The controller may be further adapted to cease heating the heating element and to reheat the heating element without a further user input.

Yet another aspect of the invention provides a device for treatment of skin conditions including a heating element adapted and configured to be placed against a skin surface to be treated; a handle area adapted and configured to be held by a user and to support the heating element when placed against the skin surface; and a heating circuit adapted and configured to heat the heating element to a temperature of at least about 67° C. for less than about 0.1 second. In some embodiments, the heating circuit includes a controller adapted and configured to control the heat generated by the heating element in response to a user input. The controller may be further adapted to cease heating the heating element and to reheat the heating element without a further user input.

In each of these aspects of the invention, the heating element could be a resistive heater, such as a thin metal resistor. The heating element may use a metal selected from the group consisting of nichrome, tungsten, aluminum, gold, copper and/or steel and may have a backing layer, an electrically insulating protective layer, and/or a high conductivity layer. A skin contact surface of the heating element may have a surface area of about 1 cm.

In each of these aspects of the invention, the heating element may be adapted to be heated to a of about 75° C.—about 100° C. or about 100° C.—about 200° C. in a period of less than about 0.5 seconds. The total energy transferred to the skin may be limited to less than about 50 $J/cm^2$ or less than about 5 $J/cm^2$. The device may also include a temperature sensor adapted and configured to sense the temperature generated by the heating element and to control the temperature of said heating element. The device may also include a cooling element adapted and configured to cool the heating element and/or a skin surface to a temperature of less than about 60° C. The device may also include a light emitting diode.

In some embodiments, the heating circuit is further adapted to heat the heating element to a temperature of at least 67° C. for less than about 0.1 second, lower the temperature of the heating element for a period of about 0.5 seconds, and reheat the heating element to a temperature of at least 67° C. for less than about 0.1 second. In some embodiments, activation of the user interface by a user heats the heating element to a peak temperature of about 250° C. in about 1 millisecond and the peak temperature decays to about 100° C. in less than about 0.5 seconds.

Still another aspect of the invention provides a method of treating a skin condition including the step of heating a skin surface of a subject to a temperature of at least about 70° C. in less than about 1 second for a time duration of less than about 1 second. Some embodiments include the step of ceasing the heating step for about ten milliseconds to about five seconds, then reheating the skin surface to a temperature of at least about 70° C. for a time duration of less than about 1 second. The ceasing and reheating steps may be repeated.

Another aspect of the invention provides a method of treating a skin condition by applying to a skin surface of a subject at least two pulses of heat to raise the skin surface to a peak temperature of at least about 70° C., the peak temperature being achieved by each pulse in a time period of less than about one second. Some embodiments include the step of providing a delay between the pulses of heat to allow the skin surface to reach a temperature of less than about 50° C. The method may also include applying a topical substance to the surface of said skin prior to, during, and/or after the application of peak temperature. The skin condition treated may be acne, a wart, a cold sore, and/or a skin wrinkle. In some embodiments, the temperature stays above about 70° C. for a period of less than about 1 second.

Yet another aspect of the invention provides a method of treating a skin condition comprising applying a heat source to a skin surface and heating the heat source to a peak temperature greater than about 67° C. for less than about 0.1 second. Some embodiments include the further step of ceasing the heating step for about ten milliseconds to about five seconds, then reheating the skin surface to a temperature of at least about 70° C. for a time duration of less than about 1 second. The ceasing and reheating steps may be repeated.

In some embodiments, the heating element comprises a resistive heater and/or a thin metal resistor. The metal in the heating element can be nichrome, tungsten, aluminum, gold, copper and/or steel. The resistive heater is preferably less than 200 μm thick and has a surface area of about 1 cm$^2$. The heating element includes in some embodiments a backing layer to add strength and to conduct heat; an electrically insulating protective layer for placement directly onto skin; a high conductivity layer for placement directly onto skin to improve temperature uniformity; and/or an electrical circuit configured to charge a capacitor that stores enough energy to heat said heating element. The controller may include a control circuit and a temperature sensor, wherein the control circuit monitors the temperature sensor and prevents the heating element from heating to a temperature that would burn human skin. In some embodiments, the device further comprises a cooling element. Typically the cooling element cools the skin and/or the heating element, preferably in between heat pulses. Further, the cooling element could ensure that the heating element is hot again heated until it and/or the skin has reached a temperature of about 50° C. or less. In other embodiments, the device further comprises a temperature sensor, such as a thermocouple, and or a battery powered light emitting diode attached to the housing to provide illumination.

Another aspect of the invention is a device for delivering a controlled amount of thermal energy to tissue comprising a resistive heating element, a circuit to deliver a fixed amount of energy to the resistive heating element, and an element to activate and trigger the circuit. Preferably, the device further comprises a thin insulating layer placed between the resistive heating element and the surface of the targeted skin. The device preferably heats the skin quickly to a temperature greater than about 50° C. Another embodiment is a device for treating the skin comprising a thermoelectric cooler adapted and configured to contact a skin surface, a circuit to deliver a controlled amount of energy to said thermoelectric cooler, an element to activate and trigger the circuit. In a preferred embodiment, the device further comprises an element adapted and configured to reverse the polarity of the thermoelectric cooler so that after being heated for a period of time, the hot plate of the thermoelectric cooler becomes a cold plate, and is allowed to cool the surface of the skin for a second period of time. In one embodiment, the device further comprises a plurality of thermoelectric coolers so that a spatial and temporal heating and cooling configuration is tailored at the targeted skin surface. Preferably, the device heats the surface of the skin to a peak temperature in excess of about 50° C. for a duration of about 0.5 second or less. In some embodiments, the devices described herein heat to a peak temperature of about 200° C. and this peak temperature is maintained for less than about 5 seconds, preferably for less than about 1 seconds.

In one embodiment, the invention is a device for treatment of skin conditions comprising a heating element adapted and configured to heat to a peak temperature of at least about 70° C. in a period of less than about one second, to maintain said peak temperature for a period of less than one second, and to contact a skin-surface; and a controller adapted and configured to control the heat generated by said heating element in response to a user input. This device can further include a housing for the heating element and controller, said housing being capable of being held in the hand of a user.

In another embodiment, the invention is a device for treatment of skin conditions comprising a housing adapted and configured to be held in the hand of a user, said housing comprising a heating element adapted and configured to heat to a peak temperature of at least about 70° C. in a period of less than about one second, to maintain said peak temperature for a period of less than one second, and to contact a skin surface; a controller adapted and configured to control the heat generated by said heating element in response to a user input; a power source; and a user interface adapted and configured to be managed by a user to control said heating element.

Yet another embodiment of the invention is a device for treatment of skin conditions comprising a heating element adapted and configured to be placed against a skin surface to be treated; a handle area adapted and configured to be held by a user and to support the heating element when placed against the skin surface; and a heating circuit adapted and configured to heat the heating element to a peak temperature of at least about 67° C. for less than about 0.1 second.

The devices described herein can include a temperature sensor adapted and configured to sense a heat generated by said heating element and to control the heat generated by the heating element. They can also include a cooling element adapted and configured to cool said heating element and/or a skin surface to a temperature of less than about 60° C. In a preferred embodiment, the device includes a heating circuit adapted to heat the heating element to a temperature of at least 67° C. for less than about 0.1 second, lower the temperature of the heating element for a period of about 0.5 seconds, and reheat the heating element to a temperature of at least 67° C. for less than about 0.1 second. In another preferred embodiment, upon activation of the device by a user the heating element is heated to a peak temperature of about 250° C. in about 1 millisecond and said peak temperature decays to about 100° C. in less than about 0.5 seconds.

Another aspect of the invention is methods of use of the devices of the present invention in the treatment of skin conditions, such as acne, warts, and skin wrinkles. In a preferred embodiment, the device is used in combination with topical agents used in the treatment of skin conditions. This topical agent can be applied by the user or can be applied with the devices described herein. The present invention can also be combined with acne treatment creams and gels to further accelerate treatment. For example, creams or gels containing benzoyl peroxide could be applied before or after applying the device. A preferred method of the invention is a method of treating a skin condition comprising heating a skin surface of a subject to a peak temperature of at least about 70° C., wherein said peak temperature is achieved within a time period of less than about 1 second and said heating is for a time duration of less than about 1 second. Another preferred method is a method of treating a skin condition comprising applying to a skin surface of a subject at least two pulses of heat to raise the skin surface to a peak temperature of at least about 70° C., said peak temperature being achieved by each pulse in a time period of less than about one second. There can be a delay between the pulses of heat to allow the skin surface to reach a temperature of less than about 50° C. Preferably in the methods the peak temperature is maintained for a period of less than about 1 second. One preferred embodiment is a method of treating a skin condition comprising applying a heat source to a skin surface and heating the heat source to a temperature greater than about 67° C. for less than about 0.1 second. This method can further comprise ceasing the heating step for a period of about 0.5 seconds and heating the heat source to a temperature greater than about 67° C. for less than about 0.1 second.

Other objects and advantages of the present invention will become apparent from the following description and accompanying drawings.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 8 depicts temperature time history at different tissue depths from surface for a single heating pulse.

FIG. 9 depicts temperature time history at different tissue depths from surface for two heating pulses (0 and 2.0 secs) with the same total energy as FIG. 8.

DETAILED DESCRIPTION OF THE INVENTION

Figure 5:
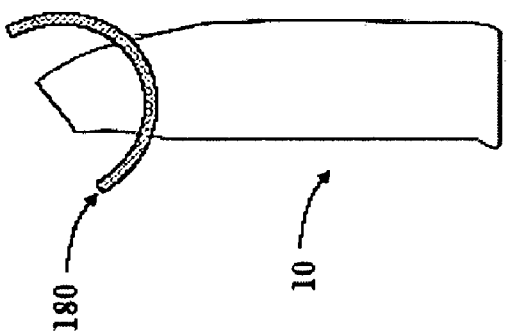
FIG. 5 shows another embodiment of the handheld acne treatment device that integrates a protective shield.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

The present invention is a compact hand held device that can be safely used by adolescents and adults suffering from skin conditions and skin lesions, such as acne, blemished skin or fine wrinkles. In one embodiment, the present invention comprises a hand held device with an input device such as an on/off switch and a button that activates the device when it is placed on the target site. In one embodiment, activation of the device allows application of heat pulses to the affected area of the skin. A battery within the device powers a circuit board and drives a short pulse of current through a thin film resistor. In one embodiment, the thin film resistor heats up to approximately 300° C. in less than 0.1 sec. Thermal conduction transfers the heat to the skin and causes a biological response that accelerates acne clearing. The total energy transferred is low enough to prevent burns, typically less than about 50 $J/cm^2$ and for most applications less than about 5 $J/cm^2$. Preferably the energy transferred to the skin is less than about 60 $J/cm^2$, less than about 55 $J/cm^2$, less than about 50 $J/cm^2$, less than about 45 $J/cm^2$, less than about 40 $J/cm^2$, less than about 35 $J/cm^2$, less than about 30 $J/cm^2$, less than about 25 $J/cm^2$, less than about 20 $J/cm^2$, less than about 15 $J/cm^2$, less than about 10 $J/cm^2$, or less than about 5 $J/cm^2$. The energy transferred to the skin can be about 5 $J/cm^2$ to about 10 $J/cm^2$, about 10 $J/cm^2$ to about 15 $J/cm^2$, about 15 $J/cm^2$ to about 20 $J/cm^2$, about 20 $J/cm^2$ to about 25 $J/cm^2$, about 25 $J/cm^2$ to about 30 $J/cm^2$, about 30 $J/cm^2$ to about 35 $J/cm^2$, about 35 $J/cm^2$ to about 40 $J/cm^2$, about 40 $J/cm^2$ to about 45 $J/cm^2$, about 45 $J/cm^2$ to about 50 $J/cm^2$, or about 50 $J/cm^2$ to about 60 $J/cm^2$. In another embodiment, of the present invention ultrabright LEDs are integrated into the device to provide illumination in the blue or red spectral range to improve treatment.

The devices described herein utilize light energy, heat energy, or a combination of the two for selective surface heating that allows the user to achieve temporary pore enlargements for cleaning of the skin pores and expulsion of unwanted debris and undesired substances filling the pores, thus reducing the size of unseemly pores and enhancing the health and appearance of the skin. The method also contemplates thermal energy and/or light energy deposition into the skin to allow selective injury to the upper layers of the skin and new, more elastic collagen production. The device described herein is also designed to allow treatment of the skin more effectively with possibly lower doses of rejuvenating agents. Not intending to limit the mechanism of action, it is believed that the controlled damage to the epidermis and upper layers of the dermis result in new collagen production and dual action via the use of a combined optothermal heating and enhanced absorption. The present invention includes a compact hand held device that can be safely used by adolescents and adults wishing to improve the texture and appearance of their skin and to minimize the appearance of acne, blemished skin, or fine wrinkles. In one embodiment, the invention is a hand held device that can be used safely to heat a controlled layer of the skin to allow skin rejuvenation and collagen regeneration without collateral damage to adjacent tissue and while enhancing skin condition and appearance. The thin film resistor heats up with sufficient energy to cause skin rejuvenation and induce a biological response improving the appearance of the skin. In some embodiments, the energy delivery duration is less than about 0.7 sec. Thermal conduction transfers the heat to the skin and causes a biological response that enhances skin appearance; The total heat energy transferred is low enough to prevent burns, typically less than about 50 J/cm² and for most applications less than about 10 J/cm².

In another embodiment, of the present invention the thin film resistor is replaced with an optical absorbing layer that is heated by flash lamps within the device. The flash lamps are fired by a short discharge, which produces broadband (white) light. Depending on the desired final temperature of the optical absorbing layer one or multiple flash lamps can be fired simultaneously to combine their light under a single reflector directing the light into the target skin. Alternatively, lamps can be fired in sequence to result in broader longer pulse duration of energy. Again, thermal conduction transfers the heat to the skin and causes a biological response that enlarges pores to enhance product or medicine delivery, clear acne, induce rejuvenation of the skin, and produce new collagen. The total heat transferred is low enough to prevent burns, typically less than about 50 J/cm² and for most applications less than about 10 J/cm². In this embodiment, the absorbing layer can be designed to allow some light to be transmitted. For example, blue or UV light could be transmitted to interact directly with tissue and kill bacteria directly.

When heat is used in the treatment of skin conditions, the heat may be applied in a pulsing or a non-pulsing manner. Preferably, the temperature used in the treatment is greater than about 67° C. The preferable range of temperatures is from about 67° to about 400° C. In a preferred embodiment, the high temperatures disclosed herein can be applied to the skin without causing burns as the temperatures are applied for short periods of time, in one embodiment, e.g., for less than about 1 second. The temperatures described herein could be the temperature of the heating element of the device being used and/or could be the temperature at the site of application on the skin. Typically, when the contact between the heating element and the surface of the skin is good, the temperature of the heating element is the same as the temperature on the surface of the skin. Another preferred range of temperature is from about 100° C. to about 400° C. Yet another preferred range is about 75° C. to about 200° C. In one embodiment, the heating element reaches a temperature of about 90° C. to about 100° C. within a time period of less than about 0.05 seconds, then permitted to cool through thermal conduction into the skin. One manner of application of pulsed heat with a heating element applied to the skin is as follows—the heating element is raised to a temperature of at least about 200° C. in less than about 0.5 seconds, then permitted to cool for about 1-5 seconds, and then raised to at least about 130° C. in about 0.5 seconds. This pulsing can be repeated as necessary. Preferably the peak temperatures achieved are greater than about 67° C., greater than about 70° C., greater than about 75° C., greater than about 80° C., greater than about 85° C., greater than about 90° C., greater than about 100° C., greater than about 125° C., greater than about 150° C., greater than about 175° C., greater than about 200° C., greater than about 225° C., greater than about 250° C., greater than about 300° C., greater than about 350° C., greater than about 400° C., and greater than about 450° C. Also, the peak temperatures achieved are less than about 67° C., less than about 70° C., less than about 75° C., less than about 80° C., less than about 85° C., less than about 90° C., less than about 100° C., less than about 125° C., less than about 150° C., less than about 175° C., less than about 200° C., less than about 225° C., less than about 250° C., less than about 300° C., less than about 350° C., less than about 400° C., and less than about 450° C.

In one embodiment, the time for achieving the heating element peak temperature (and, therefore, the skin surface peak temperature) in both the pulse and/or non-pulse applications is from about less than about 1 second to about 3 seconds. Preferred times include about 0.05 second, about 0.1 second, about 0.2 second, about 0.3 second, about 0.4 second, about 0.5 second, about 0.6 second, about 0.7 second, about 0.8 second, about 0.9 second, about 1 second, about 1.5 second, and about 2.0 second.

In some embodiments, the temperature of the heating element is permitted to decay from its peak temperature such that the duration of heat application (i.e., the time period during which the heating element temperature is above a target value) in both the pulse and/or non-pulse embodiments is from about less than about 1 second to about 3 seconds. Other possible durations include about 0.05 second, about 0.1 second, about 0.2 second, about 0.3 second, about 0.4 second, about 0.5 second, about 0.6 second, about 0.7 second, about 0.8 second, about 0.9 second, about 1 second, about 1.5 second, and about 2.0 second. In the pulsed embodiments, the time periods between each heat pulse could be the same or could be different.

When the heat is applied the skin in pulses, the heating element is preferably allowed to cool before application of the next pulse of heat. Preferably, the cooling is to about less than about 20° C., less than about 25° C., less than about 30° C., less than about 35° C., less than about 40° C., less than about 45° C., less than about 50° C., less than about 55° C., less than about 60° C., less than about 65° C., less than about 70° C., less than about 75° C., and less than about 80° C. Preferred time periods between pulses include less than about 5 seconds, less than about 4 seconds, less than about 3 seconds, less than about 2 seconds, or less than about 1 second.

Devices

Figure 1:
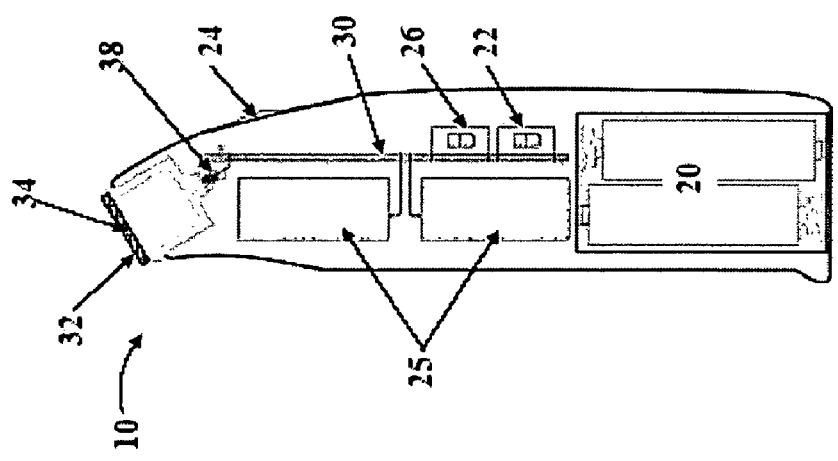
FIG. 1 shows a sectional view taken through the handheld acne treatment device that uses a thin film resistor to deliver energy into the skin.

FIG. 1 shows a cross-sectional view of one embodiment of a hand held treatment device 10. The device consists of a battery 20 that powers device control elements on a circuit board 30. The circuit board 30 is activated with power switch 22 or other user input device to charge a capacitor 25 that stores enough energy to heat a heating element (e.g., a thin resistive heater) 32 to the necessary temperatures (of about 70° C. to about 400° C.) and to maintain a temperature (although not necessarily a constant temperature) above about 70° C. to about 400° C. for the required duration. The capacitor 25 is automatically discharged through the resistor 32 when button 24 is pushed. The circuit will then recharge the capacitor and be ready to fire again within a few seconds. In order to reduce the risk of accidental burns, the heating element is allowed to cool before another heating pulse can be fired. When used in a multi-pulse mode, the device delivers multiple heat pulses automatically without further user input. In one embodiment, a temperature sensor (e.g., thermocouple) 34 monitors the temperature of the heating element and interacts with a controller on the circuit board 30 to prevent a second heating pulse until the temperature drops below an acceptable temperature (e.g., about 40° C.). The thin resistive heater is typically made of metal (e.g., Nichrome (Nickel and Chromium alloy), tungsten, aluminum, copper, gold, steel) and is typically less than 200 µm thick. Suitable thin film resistors can also be found at Minco Products, Inc. (http://www.minco.com/) (e.g., Thermofoil™ heaters). Other suitable thin film resistors are available from Kyocera, Inc.

In one embodiment the user can select different power levels or multi-pulse heating formats. For example, as shown in FIG. 1, a high and low power setting can be selected using button 26. Alternatively, a single push button could be used to power the device and select operating modes. For example, pressing the button turns on the device at a low setting, pressing it again changes to high power setting, pressing it a second time changes to a multiple pulse heating format. Each time the button is pressed it cycles through all the possible modes. The current mode can be displayed by a series of LED's or a small LCD.

An optional LED 38 can also be integrated into the device to provide illumination and aid in treatment. For example blue and red light have been shown to treat acne. Rather than high/low, and off/on switches, the device can use a single button to select the desired operating mode. For example, pressing the button for more then 1 second turns device on or off. Pressing the button for a short time when on causes the device to switch the operating mode. This allows the device to operate in a wide variety of modes including complex multi-pulse sequences.

Figure 2:
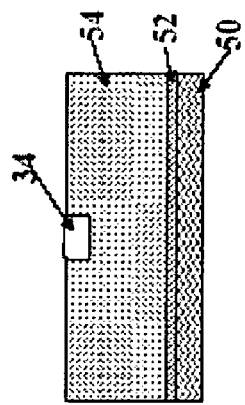
FIG. 2 shows a sectional view taken through one embodiment of the heating element, which includes a thick backing layer.
Figure 3:
FIG. 3 shows a sectional view taken through another embodiment of the heating element.
Figure 4:
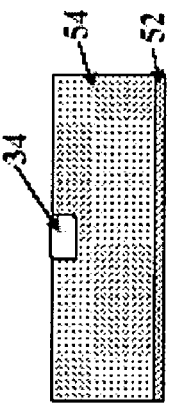
FIG. 4 shows a sectional view taken through another embodiment of the heating element.

FIGS. 2, 3, and 4 show exemplary embodiments that may be substituted for the heating element 32. A thick backing layer 54, shown in FIGS. 2 and 4, can be used to add strength to the heating element and also conduct heat away from the thin resistive heater 52. In one embodiment, a thin protective layer 50 covers the resistive heater. In the preferred embodiment, the protective layer 50 is an electrical insulator and has good thermal conductivity. This protective layer 50 reduces the risk of shock to the user and can act to improve temperature uniformity across the surface of the heating element. Alternatively the thin resistive heater 52 can be chemically treated (e.g., anodized) to provide a very thin insulating layer to prevent electrical shock to the user. For most applications the thin resistive heater 52 and optional protective layer 50 are less than 500 µm thick to limit the total energy required to heat the material to the necessary peak temperature. This also limits the maximum energy that can be transferred into the tissue thereby reducing the risk of burns. A temperature sensor 34, shown in FIGS. 2 and 4, can be integrated into the backing layer 54 to monitor temperature. For most applications the surface area of the skin contacting surface of the heating element is approximately 1 $cm^2$.

The heating element in the present invention will quickly cool by thermal conduction into tissue (and if present into the backing layer as well). The maximum energy that can be transferred to the skin is controlled by the peak temperature and the thickness of the heated layer. For example, for a 100 µm thick absorbing glass layer heated to 300° C. the available energy to transfer to tissue that is at 30° C. is approximately 5.7 $J/cm^2$. For pulsed heating of a thin heater the cooling time can be estimated from the thermal relaxation time, $\tau=(\Delta x/\pi)^2 \rho c/\kappa$ where $\Delta x$ is the thickness, $\rho$ is the density, $c$ is the specific heat, and $\kappa$ is the thermal conductivity of heater. For glass, the relaxation time is approximately 1.2 msec. For a 100 µm thick copper layer heated to 300° C. the available energy to transfer to tissue that is at 30° C. is approximately 9.2 $J/cm^2$. The relaxation time is approximately 8.65 µsec. By appropriate selection of the heating pulse format and heater materials the peak tissue temperature and time history can be controlled. FIG. 5 shows another embodiment of the handheld acne treatment device that integrates a protective shield 180 to prevent the user from positioning the device on the eye.

Figure 6:
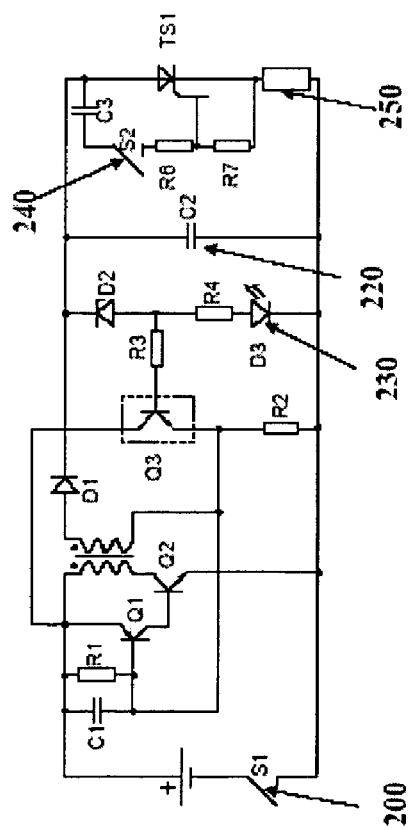
FIG. 6 shows one possible circuit diagram for pulsing the thin film resistor.

FIG. 6 shows one possible circuit to pulse the thin resistive heater to the desired peak temperature. A switch 200 (S1) is turned on to activate the device and charge the capacitor 220 (C2). When the capacitor is fully charged, a lamp 230 LED (D3) turns on and the device is ready to fire. When the fire switch 240 (S2) is activated, it turns on the thyristor (TS1) and discharges the capacitor 220 through the thin resistive heater 250. In a preferred embodiment the discharge through the thin resistive heater has a time constant of less than 10 ms. The capacitor 220 begins to charge again after firing and after several seconds (depending on battery and resistance) is fully charged. This circuit releases a maximum energy per pulse of ½ $CV^2$ where C is the capacitor capacitance and V is the final voltage across the capacitor. By selecting appropriate values of C and V, the released energy can be kept below the threshold for tissue burns.

Figure 7:
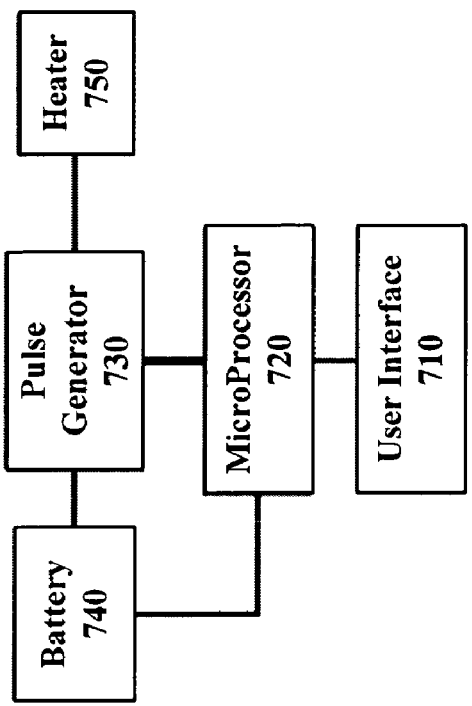
FIG. 7 shows a block diagram for a device that uses a microprocessor to allow the user to apply different sequences of heating pulses.

FIG. 7 shows a block diagram of the key elements in the control electronics of an alternative circuit to control heating of the resistive heater. A user interface 710 that could include buttons, switches, or touch screens are used to select the operating mode of the device and generate a pulse. The user interface 710 is input into a microprocessor 720 (e.g. PIC16F676 by Microchip inc.) that controls all the functions of the pulse generator 730. Power is provided by a battery 740 or directly from a power supply. The pulse generator 730 converts the voltage from the battery 740 to a high voltage that can be used to charge a capacitor that discharges through the heater 750 when the user presses a fire button. Typically the discharge through the thin resistive heater 750 has a time constant of less than 100 ms. A maximum energy per pulse of ½ $CV^2$ where C is the capacitor capacitance and V is the final voltage across the capacitor. By selecting appropriate values of C and V, the released energy can be kept below the threshold for tissue burns. The microprocessor 720 controls the charging and firing of the device directly based on user input. The user can select power and multi-pulse heating formats that can deliver heat deeper into tissue while preventing burns.

The possible pulse formats that can be produced include a series of constant energy pulses with a separation of less than about 2 seconds that could maintain a near constant temperature below the skin surface. A decaying pulse series with each successive pulse having a lower energy can also be used. An increasing pulse series with each successive pulse having a higher energy can also be used. By carefully adjusting the pulse series and per pulse energy, the peak tissue temperature and temperature profile inside tissue can be controlled to prevent burns. In preferred embodiments, the separation between pulses is greater than 10 ms but less than 5 seconds.

FIG. 8 shows the calculated temperature history 0.2, 0.5 and 1.0 mm below the surface when a single heating pulse is applied at time equal 0. The high peak temperatures exist for less than 0.1 seconds which limits the risk of burns.

FIG. 9 shows the calculated temperature history 0.2, 0.5 and 1.0 mm below the surface when two heating pulses are applied to the heater. The first pulse has higher total energy and produces a peak temperature of 180° C. Two seconds later a second pulse with one half of the energy of the first pulse reheats the thin metal heater. The resulting temperature inside the tissue is higher than that produced by the single pulse with an equal total energy. The multi-pulse capability allows the device to heat more tissue without exceeding the burn threshold which is a function of the peak temperature.

The short time duration of the high peak temperature is critical to preventing skin burns. Henriques (F. C. Henriques, "Studies of Thermal Injury: The Predictability and the Significance of Thermally Induced Rate Processes Leading to Irreversible Epidermal Injury", Archives of Pathology, 43, 5 May 1947, Pages 489-502) published a theory on skin burns based on a form of the Arrhenius equation for heat induced irreversible chemical reaction. Although numerous other studies have investigated the burn process, the conclusions are similar. A skin burn occurs as a result of thermally induced changes in protein structure that have an activation energy of about 600 MJ/kg-mol. For skin the Henriques Integral equation can be written as:

$$\omega = \int_0^t e^{226.78 - \frac{75000}{T}} dt$$

where T is the temperature in Kelvin at depth x and is a function of time, and $\omega$ is a function of burn injury. Integration is carried out over the time the basal layer temperature is greater then or equal to 44° C. Second degree burns occur when $\omega=1$. First degree burns occur for values of $\omega=0.53$. Third degree burns occur at a critical value of $\omega=1$ at the base of the dermis. For the present device under normal operation, $\omega<0.4$ for depths greater than 100 μm below skin surface. For this reason the risk of burn is very low.

Figure 10:
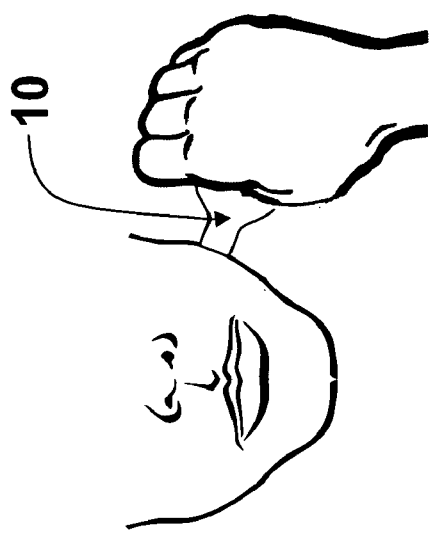
FIG. 10 shows how the device might be used to treat a blemish on the face.

FIG. 10 shows how the present invention would be used to treat a blemish on the face. The device 10 is activated and then placed in contact with the skin. When the device 10 is in good contact and fully charged, the fire button is pressed to deliver energy to the heating element, which then transfers its energy to the skin. The thermal impulse to the skin acts to open pores and accelerate clearing of the blemish. In some cases, multiple treatments in one session may be necessary to effectively treat the blemish. In this case the minimum time between treatments is controlled by the circuit, which prevents misuse and possible burns. It may also be necessary to perform multiple treatments through the course of a day, or week to treat some blemishes.

In another embodiment of the handheld acne treatment device the control electronics have a mode of operation in which the thin film resistor is pulsed with multiple current pulses to produce a desired heating profile. For example, the device is first pulsed to a high temperature as previously described; one to five seconds later a second pulse of possibly lower current is produced to reheat the thin film resistor. Additional pulses can be produced with user selected delay between the pulses and variable peak temperature (or energy). Using multiple pulses can allow the user to achieve higher temperatures below the skin without burning the skin.

Not intending to limit the mechanism of action—the present invention envisions a plurality of skin improvement effects by the methods of the present invention:

By depositing a controlled amount of thermal energy at the surface and allowing the energy to flow into the upper layer of the dermis to achieve controlled damage to the collagen in the upper dermal layer. Possibly a cooling element can be activated after a predetermined time of surface heating to remove thermal energy from the surface of the skin, protect the surface of the skin from a lengthy exposure to thermal energy, and reverse the flow of thermal energy from deeper lying layers in the dermis back to the surface.

By temporarily enlarging skin surface pores and allowing cleansing of the pores and causing expulsion of unwanted debris, dirt, and contaminants thus resulting in reduced pore size.

By temporarily enlarging skin surface pores thus allowing nutrients, conditioners, and possibly medications to flow into deeper layers of the skin.

By temporarily enlarging skin surface pores and allowing the expulsion of harmful sebum and bacteria thus reducing the chance for the development of acne and other sebaceous gland related ailments.

By thermally damaging the surface layers of the skin followed by flaking and removal of portions of the stratum conium, and portions of the epidermis and dermis.

By thermally damaging vascular or a pigmented component of the skin near the skin surface (in the epidermis or upper dermis). These unwanted damaged components will then be removed by the body as waste products eliminating disfiguring skin blemishes.

Method of Use

The devices described herein are suitable for use in the treatment of various skin conditions and lesions. Examples of such skin conditions and lesions are provided herein, but are not limited to the conditions and lesions described herein. Bacterial and fungal skin infections lead to common lesions such as acne, pimples and under-nail fungal infections. Other lesions are caused by irritants, which may be introduced as a result of bug bites or by exposure to other natural or man-made skin irritants. Still other skin lesions are caused by viral infection, a common example being the lesions known as "cold sores" or "fever blisters."

Other skin conditions include pustular eruptions, localized abscessed formation and local inflammatory conditions of the dermis and epidermis. One of the most common afflictions of this type are lesion caused by the condition known as acne vulgaris. Acne vulgaris is associated with the Gram-positive anaerobic bacterium, *Propionibacterium acnes*. Abscess formation can also occur from a number of primarily bacterial species (commonly *Staphylococcus* and *Streptococcus*) as well as fungal species, such as *dermatophytes*.

A further type of skin lesions are viral skin lesions such as cold sores, also known as fever blisters. Cold sores are usually caused by strains of the Herpes Simplex virus and commonly result in lesions on and near the lips and inside the mouth of an infected individual.

A further type of skin lesion are fungal infections, also known as fungal dermatitis, including conditions known medically as *Tinea corporis, Tinea pedis, Tinea unguium, Tinea capitis, Tinea cruris*, and *Tinea barbae*. Particularly troublesome is the condition known as *Tinea unguium* which is a fungal infection occurring under toenails or fingernails, a condition also referred to medically as onychomycosis or ringworm of the nails. Onychomycosis may be caused by several types of fungi, including *Trichophyton mentagrophytes, Candida albicans* or *Trichophyton rubrum*.

*Tinea corporis*, also known as *tinea circinata* or *tinea glabrosa* and referred to generally as ringworm of the body, is a fungal infection or dermatophytosis of the glabrous skin, i.e., areas of skin other than bearded area, scalp, groin, hands and feet, generally caused by fungal species such as those of *Microsporum* such as *Microsporum canis, Trichophyton* such as *Trichophyton rubrum, T. Mentagrophytes*, and *Epidermophyton*, particularly by the fungal species of *Trichophyton* and *Epidermophyton*. The condition generally includes the presence of one or more well-demarcated erythematous, scaly mascules with slightly raised borders and central healing, producing annular outlines. Various other types of lesions may also occur, such as those that are vesicular, eczematous, psoriasiform, verrucous, plaque-like, or deep.

*Tinea cruris*, also referred to generally as "jock itch" or ringworm of the groin, is a fungal infection or dermatophytosis of the groin, perineum and perineal regions, generally seen in males, and sometimes spreading to contiguous areas, generally caused by fungal species such as those of *Microsporum, Trichophyton*, and *Epidermophyton*, particularly by the fungal species of *Trichophyton* and *Epidermophyton*. The condition generally includes severely pruritic, sharply demarcated lesions with a raised erythematous margin and thin, dry scaling. *Tinea cruris* often accompanies *tinea pedis* (also known as "athlete's foot").

*Tinea pedis* results in interdigital lesions. Athlete's foot is an itching, malodorous, uncomfortable disorder resulting from large numbers of ordinary, nonvirulent bacteria proliferating in the fungus infected interspace.

Certain insect bites and contact with certain plants can expose skin to irritants that result in an itchy or painful immune response. The symptoms generally manifest soon after the introduction of the irritant, but can persist or sporadically reoccur for extended periods of time when the irritant is not effectively removed or inactivated by the immune response.

The invention relates to methods and devices for the treatment of skin conditions and skin lesions involving the application of thermal energy to the infected or irritated tissue. The invention can be used to treat skin lesions caused by bacterial, fungal or viral infections through the application of an amount of heat. A skin condition or skin lesion that can be treated according to the present invention is any infected or irritated tissue that can be effectively treated by the application of heat.

The lesions can be the result of infection by a bacterial strain including but not limited to strains such as *Propionibacterium acnes, Staphylococcus* species or *Streptococcus* species. In preferred embodiments, the present invention provides methods and devices for the treatment of skin lesions such as the kind commonly associated with acne vulgaris. These skin lesions include pustular eruptions and localized abscesses such as cysts, nodules, pustules, papules, comedones (blackheads) and the like. These lesions include those that are commonly referred to as pimples, whiteheads, zits, acne and the like.

Alternatively or additionally, the lesions can further be result of infection by fungal species, including but not limited to fungal species capable of producing conditions such as toenail or fingernail infections, ringworm and the like. These fungal species include *Microsporum* species such as *Microsporum canis, Trichophyton* species such as *Trichophyton rubrum, Trichophyton. Mentagrophytes, Epidermophyton* species, *Candida albicans*, and the like. Such fungal species are sometimes referred to broadly as "dermatophytes".

Alternatively or additionally, in other embodiments, the skin lesions can be the result of viral infections, including infections caused by Herpes viruses such as Herpes simplex types I and II (cold sores and genital herpes), *Varicella zoster* (chicken pox) and the like.

Alternatively or additionally, embodiments of the present invention provide methods and devices for the application of heat for the treatment of skin lesions caused by an irritant. Common skin irritants that can be treated by the present invention include those introduced by bug bites, such as mosquito, chigger, ant, spider bites, scabies and the like. Other skin irritants introduced by other animal species, such as jellyfish, snakes and the like, or by plants such as poison ivy, poison oak, poison sumac and the like, can also be treated using the methods and devices of the present invention.

For the purposes of the present invention "treating" a skin lesion or condition means to slow, halt or even reverse the development of skin lesions or conditions and to reduce the lesion's or condition's healing time. Therapeutic benefit can be achieved by eradication or amelioration of the underlying disorder being treated, e.g., eradication or amelioration of the acne, and/or eradication or amelioration of one or more of the physiological or psychological symptoms associated with the condition being treated, notwithstanding that the patient may still be afflicted with the underlying disorder. The terms "subject" and "animal subject" used herein typically refer to a human, but could also include other suitable animals.

EXAMPLE

Treatment of Acne with Heat

Figure 11:
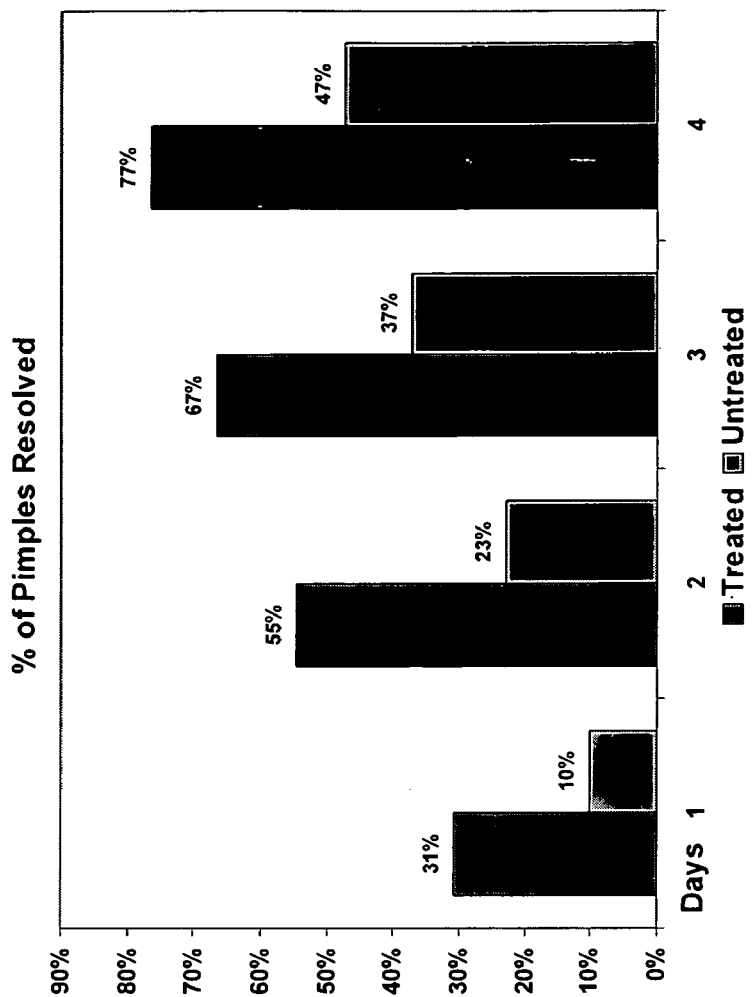
FIG. 11 depicts the effect on the healing of acne following the treatment with heat.

FIG. 11 shows the results of a clinical trial in which the device was used to treat mild to moderate acne. The study consisted of tracking the progress of treated and untreated lesions (pimples) over a 5 day period. For each patient the treated and untreated lesions were randomly selected. To treat a lesion the device was applied once a day, each day to the pimple and a single pulse of heat applied. It is believed that the peak temperature applied by the device was about 250° C., with this temperature decaying to approximately 100° C. in less than 0.5 seconds. The temperature ramps up in approximately 1 millisecond. After completion of treatment on day 5, two separate investigators independently assessed the subject's overall clinical progress and determined any adverse events. Clinical evaluation was determined by documentation of the patient's acne lesions, comparing the subject's before treatment facial photos to each subsequent treatment day as well as the final $5^{th}$ day facial photos. Total number of lesions, severity, and location was documented, graded, and compared. Grading was done on a point system. Each individual facial lesion was assigned a number to grade each lesion. The following outlines the grading point system used for each individual acne lesion:

1 (one) point—Mild lesion—level with surface or skin or minimally raised lesion, minimal erythema.
2 (two) points—Moderate lesion—visible lesion, raised 1-2 mm from skin plane, moderate erythema (0.5 mm—1 mm), with or without fluctuance.
3 (three) points—Severe lesion—visible lesion, raised 2 mm or more, erythema extension >1 mm, with or without fluctuance, open or closed, may or may not be draining serous fluid.

The final score was the sum total of all graded individual lesions. The score was determined from the baseline on the first day, before treatment. Each day of treatment, all individual acne lesions were graded and the sum total determined as the patient's score for that day. The final score was determined after treatment on the final ($5^{th}$) day from the sum total grade of all individual lesions. A score of 0-1 for a lesion indicated the lesion was resolved. The results shown in FIG. 11 show that treated pimples resolve faster then untreated pimples.

The present invention can also be combined with topical gels or creams to improve treatment of acne. For example, topical gel with benzoyl peroxide can be applied after treatment with the device. For optimum results the area to be treated is first washed with mild soap or cleanser. After washing the area to be treated, the device is applied a minimum of one time and then a topical acne gel is applied. This process would usually be repeated twice a day.

The above descriptions and illustrations are only by way of example and are not to be taken as limiting the invention in any manner. One skilled in the art can substitute known equivalents for the structures and means described. The full scope and definition of the invention, therefore, is set forth in the following claims.

What is claimed is:

1. A device for treatment of skin conditions comprising:
a heating element adapted and configured to be placed against a skin surface to be treated;
a handle area adapted and configured to be held by a user and to support the heating element when placed against the skin surface; and
a heating circuit adapted and configured to heat the heating element to a peak temperature of at least about 67° C. for less than about 0.1 second, wherein said heating element comprises a backing layer, an electrically insulating protective layer, and/or a high conductivity layer.

2. A device for treatment of skin conditions comprising:
a heating element adapted and configured to be placed against a skin surface to be treated;
a handle area adapted and configured to be held by a user and to support the heating element when placed against the skin surface; and
a heating circuit adapted and configured to heat the heating element to a peak temperature of at least about 67° C. for less than about 0.1 second, wherein a skin contact surface of said heating element has a surface area of about 1 cm$^2$.

3. A device for treatment of skin conditions comprising:
a heating element adapted and configured to be placed against a skin surface to be treated;
a handle area adapted and configured to be held by a user and to support the heating element when placed against the skin surface;
a heating circuit adapted and configured to heat the heating element to a peak temperature of at least about 67° C. for less than about 0.1 second; and
a temperature sensor, said sensor being adapted and configured to sense the temperature of said heating element and to control said temperature of said heating element.

4. A device for treatment of skin conditions comprising:
a heating element adapted and configured to be placed against a skin surface to be treated;
a handle area adapted and configured to be held by a user and to support the heating element when placed against the skin surface a heating circuit adapted and configured to heat the heating element to a peak temperature of at least about 67° C. for less than about 0.1 second; and
a light emitting diode.

5. A device for treatment of skin conditions comprising:
a heating element adapted and configured to be placed against a skin surface to be treated;
a handle area adapted and configured to be held by a user and to support the heating element when placed against the skin surface; and
a heating circuit adapted and configured to heat the heating element to a temperature of at least about 67° C. for less than about 0.1 second, wherein the heating circuit is further adapted to heat the heating element to a peak temperature of at least 67° C. for less than about 0.1 second, lower the temperature of the heating element for a period of about 0.5 seconds, and reheat the heating element to a temperature of at least 67° C. for less than about 0.1 second.

6. A method of treating a skin condition comprising applying a heat source to a skin surface, heating the heat source to a peak temperature greater than about 67° C. for less than about 0.1 second,
ceasing the heating step for about ten milliseconds to about five seconds,
then reheating the skin surface to a temperature of at least about 70° C. for a time duration of less than about 1 second.

7. The method of claim 6 further comprising repeating the ceasing and reheating steps.

* * * * *